(12) United States Patent
Duvvuri et al.

(10) Patent No.: US 11,944,750 B2
(45) Date of Patent: Apr. 2, 2024

(54) BREATHING ASSISTANCE APPARATUS

(71) Applicant: INDIAN INSTITUTE OF SCIENCE, Karnataka (IN)

(72) Inventors: Subrahmanyam Duvvuri, Karnataka (IN); Pratikash Panda, Karnataka (IN); Gaurab Banerjee, Karnataka (IN); Tv Prabhakar, Karnataka (IN)

(73) Assignee: INDIAN INSTITUTE OF SCIENCE, Karnataka (IN)

( * ) Notice: Subject to any disclaimer, the term of this patent is extended or adjusted under 35 U.S.C. 154(b) by 385 days.

(21) Appl. No.: 17/220,077

(22) Filed: Apr. 1, 2021

(65) Prior Publication Data
US 2021/0308399 A1    Oct. 7, 2021

(30) Foreign Application Priority Data
Apr. 2, 2020  (IN) .............................. 202041014759

(51) Int. Cl.
| *A61M 16/00* | (2006.01) |
| *A61M 16/06* | (2006.01) |
| *A61M 16/12* | (2006.01) |
| *A61M 16/20* | (2006.01) |

(52) U.S. Cl.
CPC .......... *A61M 16/024* (2017.08); *A61M 16/06* (2013.01); *A61M 16/12* (2013.01); *A61M 16/203* (2014.02); *A61M 16/209* (2014.02); *A61M 2016/0027* (2013.01); *A61M 2202/0208* (2013.01); *A61M 2205/3334* (2013.01)

(58) Field of Classification Search
CPC ................ A61M 16/024; A61M 16/06; A61M 16/12–127; A61M 16/20–209; A61M 2016/0027–003; A61M 2202/0208; A61M 16/0057; A61M 16/0672; A61M 16/122; A61M 16/201–205
See application file for complete search history.

(56) References Cited

U.S. PATENT DOCUMENTS

| 5,954,051 A * | 9/1999 | Heinonen ........... A61M 16/202 |
| | | 128/205.24 |
| 7,044,129 B1 * | 5/2006 | Truschel ............... A61M 16/12 |
| | | 128/204.23 |
| 2011/0126832 A1 * | 6/2011 | Winter .............. A61M 16/1065 |
| | | 128/204.26 |

(Continued)

*Primary Examiner* — Joseph D. Boecker
(74) *Attorney, Agent, or Firm* — Harness, Dickey & Pierce, P.L.C.

(57) ABSTRACT

The present disclosure relates to a breathing assistance apparatus for providing a breathing assistance to a user. The breathing assistance apparatus includes a first/second source configured with a first/second buffer. The first/second fluid is controllably transferred from the first/second source to the first/second buffer using any or combination of a first/second pressure regulators and one or more first/second valves. A mixing chamber configured with the first buffer and the second buffer to receive and mix the first fluid and the second fluid. A delivery tank configured with the mixing tank to controllably receive the third fluid through one or more fourth valves and a third pressure regulator. A user feed mask having an inlet configured with the delivery tank and user's face facilitating breathing assistance to the user.

10 Claims, 3 Drawing Sheets

(56) References Cited

U.S. PATENT DOCUMENTS

| | | | |
|---|---|---|---|
| 2013/0087146 A1* | 4/2013 | Callaghan | A61M 16/0063 |
| | | | 128/204.21 |
| 2016/0287767 A1* | 10/2016 | Simmons | A61M 1/06 |
| 2019/0189322 A1* | 6/2019 | Wygnanski | H01F 7/122 |
| 2020/0395122 A1* | 12/2020 | Takehara | A61M 11/042 |
| 2021/0001075 A1* | 1/2021 | Oddo | B01D 53/0454 |
| 2021/0080311 A1* | 3/2021 | Beacham | G01F 25/10 |
| 2021/0316105 A1* | 10/2021 | Godara | A61M 16/1005 |
| 2021/0322698 A1* | 10/2021 | Cohen | A61M 16/122 |
| 2023/0122775 A1* | 4/2023 | Johnson | A61M 16/024 |
| | | | 128/204.21 |

* cited by examiner

BREATHING ASSISTANCE APPARATUS

CROSS-REFERENCE TO RELATED APPLICATIONS

This application claims priority of Indian Application No. 202041014759, filed Apr. 2, 2020. The entire disclosure of the above application is incorporated herein by reference.

FIELD

The present disclosure relates to the field of breathing assistance apparatus such as Ventilator. More particularly the present disclosure relates to less complex and cost-effective breathing assistance apparatus.

BACKGROUND

Background description includes information that may be useful in understanding the present invention. It is not an admission that any of the information provided herein is prior art or relevant to the presently claimed invention, or that any publication specifically or implicitly referenced is prior art.

Electro-mechanical ventilators are life-saving devices that enable respiration for patients unable to properly breathe on their own during conditions such as pneumonia or acute respiratory distress syndrome (ARDS). The mechanical part of the ventilator uses pneumatic devices to blend air and oxygen in a pre-determined ratio and deliver it at a certain measured pressure or volume to the patient's lungs. The electronic part of the ventilator controls the mechanical system. The two systems are connected by a series of pressure sensors and actuators, that open and close valves to enable gas flow at required rates/quantities. While accurate pressure sensors are easy to obtain, accurate oxygen and flow rate sensors and mass flow controllers are expensive and difficult to manufacture, especially during emergency situations.

A ventilator needs to precisely deliver to the distressed patient's lungs, an air/oxygen mixture at prescribed oxygen concentrations, and the delivery should be carefully made at prescribed volumes, delivery pressures, and delivery rates. Conventionally, the required precision and control is achieved by use of sophisticated sensors and controllers, specifically flow rate and oxygen concentration sensors, and mass flow controllers. These components drive up the cost and complexity of the ventilator.

There is, therefore, a need of a cost-effective ventilator which is free from above drawbacks.

OBJECTS OF THE PRESENT DISCLOSURE

Some of the objects of the present disclosure, which at least one embodiment herein satisfies are as listed herein below.

It is an object of the present disclosure to provide a ventilator that is cost effective.

It is an object of the present disclosure to provide a ventilator that is less complex and easy to use.

It is an object of the present disclosure to provide a ventilator that requires less maintenance cost.

It is an object of the present disclosure to provide a ventilator that has increased accuracy.

SUMMARY

The present disclosure relates to the field of breathing assistance apparatus such as Ventilator. More particularly the present disclosure relates to less complex and cost-effective breathing assistance apparatus.

An aspect of the present disclosure pertains to a breathing assistance apparatus for providing a breathing assistance to a user. The breathing assistance apparatus includes a first source, a first buffer operatively configured with the first source to controllably receive a first fluid from the first source. The first fluid is controllably transferred to the first buffer using any or a combination of a first pressure regulators and one or more first valves. A second source, a second buffer operatively configured with the second source to controllably receive a second fluid from the second source. The second fluid is controllably transferred to the second buffer using any or a combination of a second pressure regulator and one or more second valves. A mixing chamber operatively configured with the first buffer and the second buffer to controllably receive a first fluid and the second fluid through one or more third valves. The mixing chamber is configured to mix the first fluid and the second fluid to for a third fluid. A delivery tank operatively configured with the mixing tank to controllably receive the third fluid through any or a combination of one or more fourth valves and a third pressure regulators. A user feed mask having an inlet operatively configured with user's face facilitating breathing assistance to the user, and the inlet is operatively configured with the mixing tank to controllably receive, through any or a combination of one or more fifth valves, and one or more first sensing devices. An outlet configured to exhaust an air exhaled by the user. The outlet is configured with any or a combination of a one or more sixth valves, and one or more second sensing devices.

In an aspect, the one or more first valves, one or more second valves, one or more third valves, one or more fourth vales, one or more fifth valves, and one or more sixth valves may comprise any or a combination of flow control valve, proportion control valve, flow direction control valve, over pressure relief valve. The one or more first sensing devices, and one or more second sensing devices may comprise any or a combination of pressure sensor, flow sensor, and differential pressure sensor.

In an aspect, the breathing assistance apparatus may comprise a control system that may further comprise a processor may be operatively configured with the first source, the second source, the first buffer, the second buffer, the mixing tank, the delivery tank, the first pressure regulators, the second pressure regulators, the third pressure regulator, the one or more first valve, one or more second valves, one or more third valves, one or more fourth valves, one or more fifth valves, one or more sixth valves, one or more first sensing devices, and one or more second sensing devices, and the processor may be configured to execute a set of instructions store in memory, upon execution of which, the processor may be configured to receive: a set of first signals, from the first pressure sensing device, pertaining to a first flow pressure value of the first fluid in the first buffer. A set of second signals, from the second sensing device, pertaining to a second flow pressure value of the second fluid in the second buffer. A set of third signals, from the third pressure regulator, pertaining to a third flow pressure value of the third fluid in the mixing chamber. A set of fourth signals, from the third pressure sensing device, pertaining to a fourth flow pressure value of the third fluid in the delivery tank. A set of fifth signals, from a first differential pressure sensing device, pertaining to a first differential pressure value of the third fluid from the delivery tank. A set of sixth signals, from a second differential pressure sensing device, pertaining to a second differential pressure value of air exhaled by the user, and transmit: a set of first actuation signals, to the one or more first valves and one or more first pressure regulators, if the first flow pressure value is any of less than or greater than a pre-defined first threshold value. A set of second actuation signals, to the one or more second valves and one or more second pressure regulators, if the second flow pressure value is any of less than or greater than a pre-defined second threshold value. A set of third actuation signals, to the one or more third valves, if the third flow pressure value is any of less than or greater than pre-defined third threshold value. A set of fourth actuation signals, to the one or more fourth valves, if the fourth flow pressure value is any of less than or greater than a pre-defined fourth threshold value. A set of fifth actuation signals, to the one or more fifth valves, if the first differential pressure value is any of less than or greater than pre-defined fifth threshold value; and a set of sixth actuation signals, to the one or more sixth valves, if the second differential pressure value is any of less than or greater than pre-defined sixth threshold value. The set of first, second, third, fourth, fifth, and sixth actuating signals facilitates controlled breathing assistance to the user.

In an aspect, one or more first valve, one or more second valves, one or more third valves, one or more fourth valves, one or more fifth valves, one or more sixth valves may be associated with respective pre-defined error coefficient values measured at time of manufacturing. The processor may be configured to monitor the respective error coefficients and transmit a set of correction signals to the one or more first valve, one or more second valves, one or more third valves, one or more fourth valves, one or more fifth valves, one or more sixth valves, if measured error coefficient values are any of less than or greater than the respective pre-defined error coefficient values. The error coefficients may pertain to a timing delay in actuation of respective valves after receiving the respective set of actuation signals. The set of correction signals may pertain to adjust an actuation time of any of the valves to accordingly control the breathing assistance to the user.

Various objects, features, aspects and advantages of the inventive subject matter will become more apparent from the following detailed description of preferred embodiments, along with the accompanying drawing figures in which like numerals represent like components.

BRIEF DESCRIPTION OF DRAWINGS

The accompanying drawings are included to provide a further understanding of the present disclosure, and are incorporated in and constitute a part of this specification. The drawings illustrate exemplary embodiments of the present disclosure and, together with the description, serve to explain the principles of the present disclosure. The diagrams are for illustration only, which thus is not a limitation of the present disclosure.

In the figures, similar components and/or features may have the same reference label. Further, various components of the same type may be distinguished by following the reference label with a second label that distinguishes among the similar components. If only the first reference label is used in the specification, the description is applicable to any one of the similar components having the same first reference label irrespective of the second reference label.

DETAILED DESCRIPTION

Figure 1A:
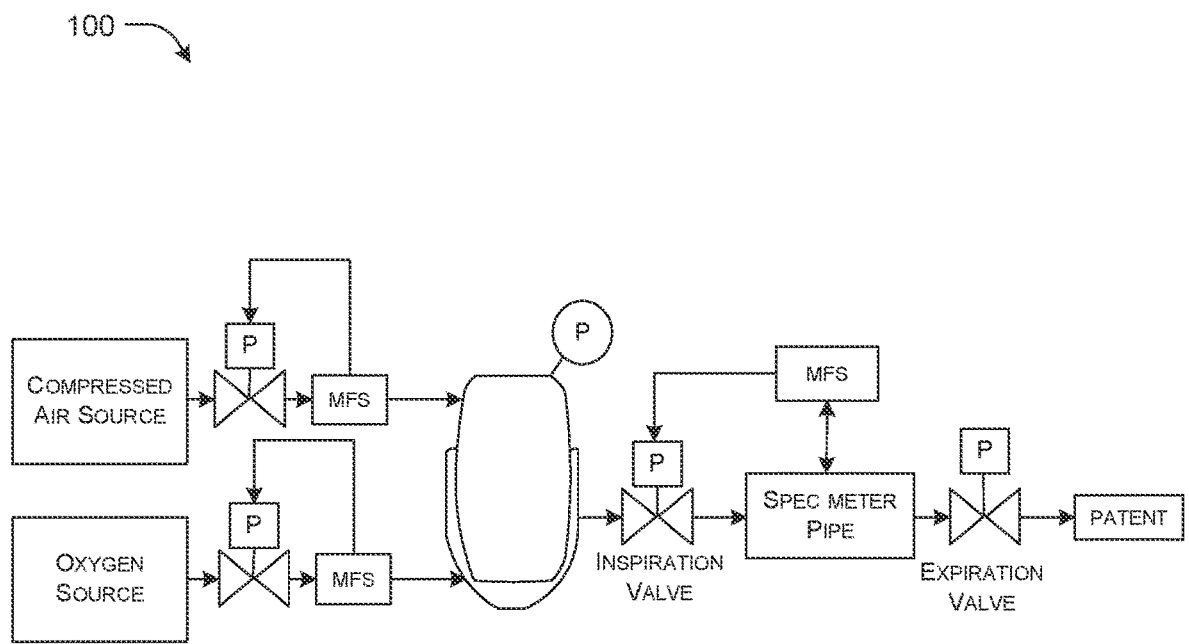
FIG. 1A illustrates a conventional breathing assistance apparatus.

The following is a detailed description of embodiments of the disclosure depicted in the accompanying drawings. The embodiments are in such detail as to clearly communicate the disclosure. However, the amount of detail offered is not intended to limit the anticipated variations of embodiments; on the contrary, the intention is to cover all modifications, equivalents, and alternatives falling within the scope of the present disclosure as defined by the appended claims.

In the following description, numerous specific details are set forth in order to provide a thorough understanding of embodiments of the present invention. It will be apparent to one skilled in the art that embodiments of the present invention may be practiced without some of these specific details.

The present disclosure relates to the field of breathing assistance apparatus such as Ventilator. More particularly the present disclosure relates to less complex and cost-effective breathing assistance apparatus.

The present disclosure elaborates upon a breathing assistance apparatus for providing a breathing assistance to a user. The breathing assistance apparatus includes a first source, a first buffer operatively configured with the first source to controllably receive a first fluid from the first source. The first fluid is controllably transferred to the first buffer using any or a combination of a first pressure regulators and one or more first valves. A second source, a second buffer operatively configured with the second source to controllably receive a second fluid from the second source. The second fluid is controllably transferred to the second buffer using any or a combination of a second pressure regulator and one or more second valves. A mixing chamber operatively configured with the first buffer and the second buffer to controllably receive a first fluid and the second fluid through one or more third valves. The mixing chamber is configured to mix the first fluid and the second fluid to for a third fluid. A delivery tank operatively configured with the mixing tank to controllably receive the third fluid through any or a combination of one or more fourth valves and a third pressure regulator. A user feed mask having an inlet operatively configured with user's face facilitating breathing assistance to the user, and the inlet is operatively configured with the mixing tank to controllably receive, through any or a combination of one or more fifth valves, and one or more first sensing devices. An outlet configured to exhaust an air exhaled by the user. The outlet is configured with any or a combination of a one or more sixth valves, and one or more second sensing devices.

In an embodiment, the one or more first valves, one or more second valves, one or more third valves, one or more fourth vales, one or more fifth valves, and one or more sixth valves can comprise any or a combination of flow control valve, proportion control valve, flow direction control valve, over pressure relief valve.

In an embodiment, the one or more first sensing devices, and one or more second sensing devices can comprise any or a combination of pressure sensor, flow sensor, and differential pressure sensor.

In an embodiment, the breathing assistance apparatus can comprise a control system that can further comprise a processor can be operatively configured with the first source, the second source, the first buffer, the second buffer, the mixing tank, the delivery tank, the first pressure regulators, the second pressure regulators, the third pressure regulator, the one or more first valve, one or more second valves, one or more third valves, one or more fourth valves, one or more fifth valves, one or more sixth valves, one or more first sensing devices, and one or more second sensing devices, and the processor can be configured to execute a set of instructions store in memory, upon execution of which, the processor can be configured to receive: a set of first signals, from the first pressure sensing device, pertaining to a first flow pressure value of the first fluid in the first buffer. A set of second signals, from the second sensing device, pertaining to a second flow pressure value of the second fluid in the second buffer. A set of third signals, from the third pressure regulator, pertaining to a third flow pressure value of the third fluid in the mixing chamber. A set of fourth signals, from the third pressure sensing device, pertaining to a fourth flow pressure value of the third fluid in the delivery tank. A set of fifth signals, from a first differential pressure sensing device, pertaining to a first differential pressure value of the third fluid from the delivery tank. A set of sixth signals, from a second differential pressure sensing device, pertaining to a second differential pressure value of air exhaled by the user, and transmit: a set of first actuation signals, to the one or more first valves and one or more first pressure regulators, if the first flow pressure value is any of less than or greater than a pre-defined first threshold value. A set of second actuation signals, to the one or more second valves and one or more second pressure regulators, if the second flow pressure value is any of less than or greater than a pre-defined second threshold value. A set of third actuation signals, to the one or more third valves, if the third flow pressure value is any of less than or greater than pre-defined third threshold value. A set of fourth actuation signals, to the one or more fourth valves, if the fourth flow pressure value is any of less than or greater than a pre-defined fourth threshold value. A set of fifth actuation signals, to the one or more fifth valves, if the first differential pressure value is any of less than or greater than pre-defined fifth threshold value; and a set of sixth actuation signals, to the one or more sixth valves, if the second differential pressure value is any of less than or greater than pre-defined sixth threshold value. The set of first, second, third, fourth, fifth, and sixth actuating signals facilitates controlled breathing assistance to the user.

In an embodiment, one or more first valve, one or more second valves, one or more third valves, one or more fourth valves, one or more fifth valves, one or more sixth valves can be associated with respective pre-defined error coefficient values measured at time of manufacturing.

In an embodiment, the processor can be configured to monitor the respective error coefficients and transmit a set of correction signals to the one or more first valve, one or more second valves, one or more third valves, one or more fourth valves, one or more fifth valves, one or more sixth valves, if measured error coefficient values are any of less than or greater than the respective pre-defined error coefficient values.

In an embodiment, the error coefficients can pertain to a timing delay in actuation of respective valves after receiving the respective set of actuation signals.

In an embodiment, the set of correction signals can pertain to adjust an actuation time of any of the valves to accordingly control the breathing assistance to the user.

In an embodiment, the mixing chamber can be configured to controllably receive the first fluid and the second fluid alternatively for a pre-defined time interval.

Figure 1B:
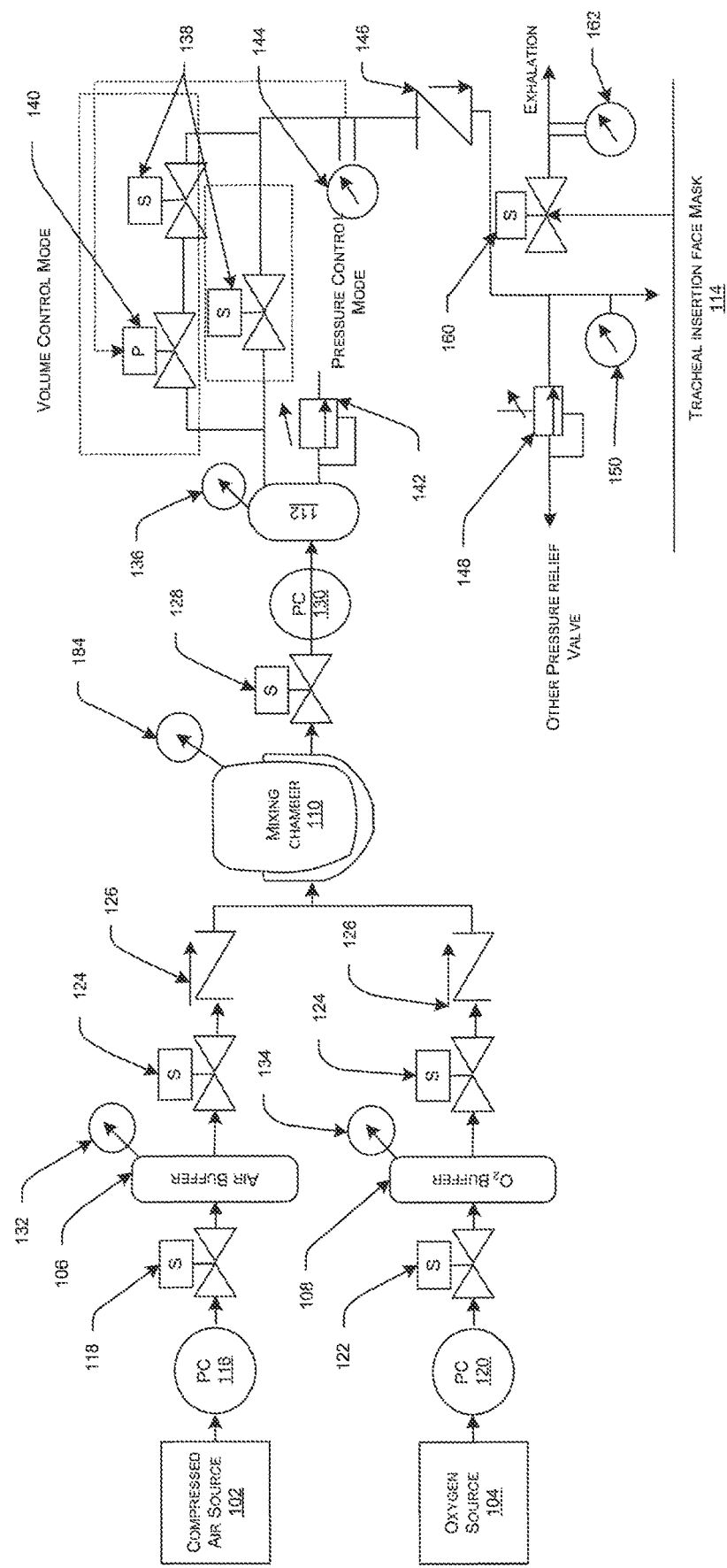
FIG. 1B illustrates an exemplary representation of breathing assistance apparatus, in accordance with an embodiment of the present disclosure.

FIG. 1B illustrates an exemplary representation of breathing assistance apparatus, in accordance with an embodiment of the present disclosure.

Figure 2:
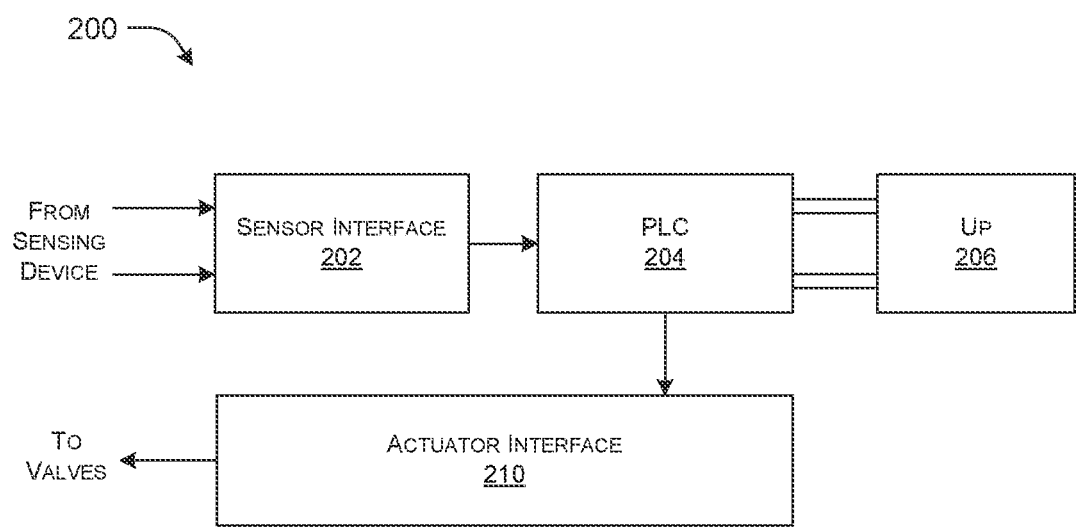
FIG. 2 illustrates exemplary block diagram of control system of the breathing assistance apparatus, in accordance with an embodiment of the present disclosure.

FIG. 2 illustrates exemplary block diagram of control system of the breathing assistance apparatus, in accordance with an embodiment of the present disclosure.

As illustrated, a breathing assistance apparatus 100 for providing a breathing assistance to a user. The breathing assistance apparatus includes a first source 102 that can be a compressed air source. A first buffer 106 can be operatively configured with the first source 102 to controllably receive a first fluid (compressed air) from the first source 102. The first buffer can include a first pressure sensor 132 (also referred as first pressure sensing device 116, herein) that can be used to measure pressure value (also referred as first pressure value, herein) of the first buffer 106 and can correspondingly generate a set of first signals. The first fluid is controllably transferred to the first buffer 106 using any or a combination of a first pressure regulators 116 and one or more first valves 118. The one or more first valves can include but not limited to solenoid ON/OFF valve.

In an embodiment, the breathing assistance apparatus can include a second source 104, and a second buffer 108 can be operatively configured with the second source 104 to controllably receive a second fluid (oxygen) from the second source 104. The second buffer 108 can include a second pressure sensor 134 (also referred as second pressure sensing device 134, herein) that can be used to measure pressure value (also referred as second pressure value, herein) of the second buffer 108 and can correspondingly generate a set of second signals. The second fluid is controllably transferred to the second buffer 108 using any or a combination of a second pressure regulator 120 and one or more second valves 122 that can be but without limiting to solenoid ON/OFF valve.

In an embodiment, a mixing chamber 110 can be operatively configured with the first buffer 106 and the second buffer 108 to controllably receive a first fluid and the second fluid through one or more third valves that can include but without limiting to solenoid ON/OFF valve 124, and one-way valve 126 (also referred as flow control valve, herein). The mixing tank 110 can include a third pressure sensor 164 (also referred as third pressure sensing device 164, herein) that can be used to measure pressure value (also referred as third pressure value, herein) of the mixing tank 110 and can correspondingly generate a set of third signals. The mixing chamber 110 can be configured to mix the first fluid and the second fluid to for a third fluid.

In an embodiment, a delivery tank 112 can be operatively configured with the mixing tank 110 to controllably receive the third fluid through any or a combination of one or more fourth valves and a third pressure regulator 130. The one or more fourth valves can include but without limiting to solenoid ON/OFF valves 128. The delivery tank 112 can include a fourth pressure sensor 136 (also referred as fourth pressure sensing device 136, herein) that can be used to measure pressure value (also referred as fourth pressure value, herein) of the delivery tank 112 and can correspondingly generate a set of fourth signals.

In an embodiment, a user feed mask 114 having an inlet operatively can be configured with user's face facilitating breathing assistance to the user, and the inlet is operatively configured with the delivery tank 112 to controllably receive the third fluid through any or a combination of one or more fifth valves, and one or more first sensing devices. The one or more fifth valves can include but not limiting to proportion control valve 140, solenoid ON/OFF valves 138, over pressure relief valves 142 and 148, one way valve 146 (also referred as flow control valve).

In an embodiment, the one or more first sensing devices can include but without limiting to differential pressure sensor 144. An outlet of the mask 114 can be configured to exhaust an air exhaled by the user. The outlet can be configured with any or a combination of a one or more sixth valves, and one or more second sensing devices. The one or more sixth valves can include but without limiting to solenoid ON/OFF valves 160, and the one or more second sensing device comprises but without limiting to differential pressure sensor 162.

In an embodiment, the breathing assistance apparatus 100 can comprise a control system 200 (can also be referred as electronic control system 200, herein). The control system 200 can include a processor 206 can be operatively configured with the first source 102, the second source 104, the first buffer 106, the second buffer 108, the mixing tank 110, the delivery tank 112, the first pressure regulators 116, the second pressure regulators 120, the third pressure regulator 128, the one or more first valve 118, one or more second valves 122, one or more third valves 124, one or more fourth valves, one or more fifth valves, one or more sixth valves 160, one or more first sensing devices 144, and one or more second sensing devices 162, through a sensor interface 202 and an actuation interface 210 that can be configured with the processor 206 through a programmable logic controller 204.

In an embodiment, the processor 206 can be configured to execute a set of instructions store in memory, upon execution of which, the processor 206 can be configured to receive using the sensing interface 202, the set of first signals, the set of second signals, the set of third signals, the set of fourth signals, the set of fifth signals, the set of sixth signals. The processor 206 can be configured to transmit a set of first actuation signals, to the one or more first valves 118 and one or more first pressure regulators 116, if the first flow pressure value is any of less than or greater than a pre-defined first threshold value. A set of second actuation signals, to the one or more second valves 122 and one or more second pressure regulators 120, if the second flow pressure value is any of less than or greater than a pre-defined second threshold value. A set of third actuation signals, to the one or more third valves 124 and 126, if the third flow pressure value is any of less than or greater than pre-defined third threshold value. A set of fourth actuation signals, to the one or more fourth valves, if the fourth flow pressure value is any of less than or greater than a pre-defined fourth threshold value. A set of fifth actuation signals, to the one or more fifth valves, if the first differential pressure value is any of less than or greater than pre-defined fifth threshold value, and a set of sixth actuation signals, to the one or more sixth valves 160, if the second differential pressure value is any of less than or greater than pre-defined sixth threshold value. The set of first, second, third, fourth, fifth, and sixth actuating signals facilitates controlled breathing assistance to the user.

In an embodiment, the mixing chamber can be configured to controllably receive the first fluid and the second fluid alternatively for a pre-defined time interval. A planned sequence of discrete fill/drain events on the air/oxygen buffer tanks (first buffer 102/second buffer 104) to achieve the required mixture ratio in the mixing tank 110. The exact mass of air/oxygen in the buffer tank at any instant can be accurately calculated by isolating the buffer tanks (close both input and output line) and making a pressure measurement then can allow to calculate the gas density (using gas laws) and thereby the total gas mass contained in the tanks (density multiplied by volume of tank). The same calculation method and steps can be repeated for the mixing tank 110 to accurately estimate the gas mass contained within the mixing tank 110.

In an embodiment, by allowing air and oxygen to flow into the mixing tank 110 from the buffer tanks (106, 108) for a finite time period, and making measurements of the initial and final buffer tank pressure (first and second pressure values) in that period, the exact mass of air and oxygen entering the mixing tank 110 can be accurately calculated. Similarly, by letting the gas mixture in the mixing tank 110 flow into the delivery tank 112 for a finite time period and making initial and final tank pressure measurements during this period can allow to calculate exact mass of mixture gas that exited the mixing tank 110 and entered the delivery tank 112. This process can be repeated indefinitely during the ventilator (also referred as breathing assistance apparatus, herein) operation to periodically replenish the delivery tank with oxygen/air mixture at the prescribed concentrations. The exact mixture ratio can be maintained by varying the time period over which oxygen from the buffer tank is let into the mixing tank relative to the time period over which air from the buffer tank is let into the mixing tank. These time periods in turn are set such that the initial and final pressures of the tanks during gas flow meet the mixture ratio requirements.

The present disclosure uses mechanical pressure regulators to set the pressure in the delivery tank such that the prescribed delivery pressure in the patient lungs is achieved. Further, by measuring the pressure drop between two locations in the patient feed line, the real-time flow rate is accurately inferred by a one-time calibration exercise (flow rate as a function of pressure drop). The control system 200 controls sequence of fill/drain events that requires precise timing, which can be made achieved using crystal referenced clocks that control the actuators operatively configured with the valves.

In an embodiment, one or more first valve, one or more second valves, one or more third valves, one or more fourth valves, one or more fifth valves, one or more sixth valves can be associated with respective pre-defined error coefficient values measured at time of manufacturing. The processor 206 can be configured to monitor the respective error coefficients and transmit a set of correction signals to the one or more first valve, one or more second valves, one or more third valves, one or more fourth valves, one or more fifth valves, one or more sixth valves, if measured error coefficient values are any of less than or greater than the respective pre-defined error coefficient values. The error coefficients can pertain to a timing delay in actuators of respective valves after receiving the respective set of actuation signals. The set of correction signals can pertain to adjust an actuation time (can also be referred as fill/drain sequence, herein) of any of the valves to accordingly control the breathing assistance to the user. The control system 200 can add precise adjustments to each actuator input in the form of time offsets to reduce the errors in critical parameters such as air/oxygen ratio, pressure and volume. This is a calibration step can also enable foreground and background calibration of the system during operation in the field and corrects it against the drift and wear and tear of components.

Further, all actuators have mechanical delays and response times, that might add finite time-offsets and consequently, errors to the fill/drain events. The electronic control system adds precise adjustments to each actuator input in the form of time offsets to reduce the errors in critical parameters such as air/oxygen ratio, pressure and volume. This is a calibration step which requires the acquisition of error coefficients during standard factory calibration. This also enables foreground and background calibration of the system during operation in the field and corrects it against the drift and wear and tear of components. When the error coefficients become too large with respect to those generated during factory calibration due to the continuous wear and tear of actuators, this information can be used as an important diagnostic tool to predict a field failure, before it actually occurs.

Moreover, in interpreting the specification, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refer to at least one of something selected from the group consisting of A, B, C . . . and N, the text should be interpreted as requiring only one element from the group, not A plus N, or B plus N, etc.

While the foregoing describes various embodiments of the invention, other and further embodiments of the invention may be devised without departing from the basic scope thereof. The scope of the invention is determined by the claims that follow. The invention is not limited to the described embodiments, versions or examples, which are included to enable a person having ordinary skill in the art to make and use the invention when combined with information and knowledge available to the person having ordinary skill in the art.

Advantages of the Invention

The proposed invention provides a cost-effective ventilator.

The proposed invention provides a ventilator that is less complex and easy to use.

The proposed invention provides a ventilator that requires less maintenance cost.

The proposed invention provides a ventilator that has increased accuracy.

What is claimed is:

1. A breathing assistance apparatus for providing a breathing assistance to a user, the breathing assistance apparatus comprising:
    a first source;
    a first buffer, having a first pressure sensing device, operatively configured with the first source to controllably receive a first fluid from the first source, wherein the first fluid is controllably transferred to the first buffer using any or a combination of a first pressure regulator and one or more first valves;
    a second source;
    a second buffer, having a second pressure sensing device, operatively configured with the second source to controllably receive a second fluid from the second source, wherein the second fluid is controllably transferred to the second buffer using any or a combination of a second pressure regulator and one or more second valves;
    a mixing chamber, having a third pressure sensing device, operatively configured with the first buffer and the second buffer to controllably receive the first fluid and the second fluid through one or more third valves, wherein the mixing chamber is configured to mix the first fluid and the second fluid to form a third fluid;
    a delivery tank, having a fourth pressure sensing device, operatively configured with the mixing chamber to controllably receive the third fluid through any or a combination of one or more fourth valves and a third pressure regulator; and
    a user feed mask having an inlet operatively configured with the user's face for facilitating breathing assistance to the user, and the inlet is operatively configured with the delivery tank to controllably receive the third fluid, through any or a combination of one or more fifth valves and one or more first sensing devices, and an outlet configured to exhaust an air exhaled by the user, wherein the outlet is configured with any or a combination of one or more sixth valves and one or more second sensing devices.

2. The breathing assistance apparatus as claimed in claim 1, wherein the first source comprises a compressed air source, and the second source comprises an oxygen source.

3. The breathing assistance apparatus as claimed in claim 1, wherein the one or more first valves, the one or more second valves, the one or more third valves, the one or more fourth valves, the one or more fifth valves, and the one or more sixth valves comprise any or a combination of flow control valve, proportion control valve, flow direction control valve, and over pressure relief valve.

4. The breathing assistance apparatus as claimed in claim 1, wherein the one or more first sensing devices, and the one or more second sensing devices comprise a differential pressure sensor.

5. The breathing assistance apparatus as claimed in claim 1, wherein the breathing assistance apparatus comprises a control system comprising:
    a processor operatively configured with the first source, the second source, the first buffer, the second buffer, the mixing chamber, the delivery tank, the first pressure regulator, the second pressure regulator, the third pressure regulator, the one or more first valves, the one or more second valves, the one or more third valves, the one or more fourth valves, the one or more fifth valves, the one or more sixth valves, the one or more first sensing devices, and the one or more second sensing devices, and the processor is configured to execute a set of instructions stored in a memory, upon execution of which, the processor is configured to receive:
        a set of first signals, from the first pressure sensing device, pertaining to a first flow pressure value of the first fluid in the first buffer;
        a set of second signals, from the second pressure sensing device, pertaining to a second flow pressure value of the second fluid in the second buffer;
        a set of third signals, from the third pressure sensing device, pertaining to a third flow pressure value of the third fluid in the mixing chamber;
        a set of fourth signals, from the fourth pressure sensing device, pertaining to a fourth flow pressure value of the third fluid in the delivery tank;
        a set of fifth signals, from the one or more first sensing devices, comprising a first differential pressure sensing device, pertaining to a first differential pressure value of the third fluid from the delivery tank;
        a set of sixth signals, from the one or more second sensing devices, comprising a second differential pressure sensing device, pertaining to a second differential pressure value of the air exhaled by the user; and transmit:

a set of first actuation signals, to the one or more first valves and the first pressure regulator, if the first flow pressure value is any of less than or greater than a pre-defined first threshold value;

a set of second actuation signals, to the one or more second valves and the second pressure regulator, if the second flow pressure value is any of less than or greater than a pre-defined second threshold value;

a set of third actuation signals, to the one or more third valves, if the third flow pressure value is any of less than or greater than a pre-defined third threshold value;

a set of fourth actuation signals, to the one or more fourth valves, if the fourth flow pressure value is any of less than or greater than a pre-defined fourth threshold value;

a set of fifth actuation signals, to the one or more fifth valves, if the first differential pressure value is any of less than or greater than a pre-defined fifth threshold value; and a set of sixth actuation signals, to the one or more sixth valves, if the second differential pressure value is any of less than or greater than a pre-defined sixth threshold value, wherein the set of first, second, third, fourth, fifth, and sixth actuating signals facilitates controlled breathing assistance to the user.

6. The breathing assistance apparatus as claimed in claim 5, wherein the one or more first valves, the one or more second valves, the one or more third valves, the one or more fourth valves, the one or more fifth valves, and the one or more sixth valves are associated with respective pre-defined error coefficient values measured at time of manufacturing.

7. The breathing assistance apparatus as claimed in claim 6, wherein the processor is configured to monitor measured error coefficient values and transmit a set of correction signals to the one or more first valves, the one or more second valves, the one or more third valves, the one or more fourth valves, the one or more fifth valves, and the one or more sixth valves, if the measured error coefficient values are any of less than or greater than the respective pre-defined error coefficient values.

8. The breathing assistance apparatus as claimed in claim 7, wherein the measured error coefficient values pertain to a timing delay in actuation of respective valves after receiving the respective set of actuation signals.

9. The breathing assistance apparatus as claimed in claim 8, wherein the set of correction signals pertains to adjusting an actuation time of any of the valves to accordingly control the breathing assistance to the user.

10. The breathing apparatus as claimed in claim 1, wherein the mixing chamber is configured to controllably receive the first fluid and the second fluid alternatively for a pre-defined time interval.

* * * * *